United States Patent [19]

Diehl

[11] Patent Number: 4,988,870
[45] Date of Patent: Jan. 29, 1991

[54] OPEN-SPLIT INTERFACE FOR MASS SPECTROMETERS

[75] Inventor: John W. Diehl, Grand Forks, N. Dak.

[73] Assignee: Und-Sem Foundation, Grand Forks, N. Dak.

[21] Appl. No.: 418,675

[22] Filed: Oct. 10, 1989

[51] Int. Cl.$^5$ .............................................. H01J 44/00
[52] U.S. Cl. .................................... 250/288; 250/281; 250/289; 73/23.37; 73/23.4
[58] Field of Search ............... 250/288, 281, 282, 789, 250/423 R; 73/23.4, 23.37

[56] References Cited

U.S. PATENT DOCUMENTS

| | | | |
|---|---|---|---|
| 1,327,252 | 1/1920 | Paulson . | |
| 2,610,023 | 9/1952 | Whitlock . | |
| 3,223,123 | 12/1965 | Young | 137/625.46 |
| 3,801,788 | 4/1974 | Milne | 250/288 |
| 3,927,693 | 12/1975 | Johnston | 137/625.47 |
| 3,939,871 | 2/1976 | Dickson | 137/625.47 |
| 4,222,412 | 9/1980 | Carle | 137/625.47 |
| 4,355,659 | 10/1982 | Kelchner | 137/625.19 |
| 4,391,778 | 7/1983 | Andresen et al. | 250/288 |
| 4,453,954 | 6/1984 | Kolb et al. | 250/198.2 |
| 4,570,068 | 2/1986 | Sakairi et al. | 250/288 |
| 4,705,616 | 11/1987 | Andresen et al. | 250/288 |
| 4,740,695 | 4/1988 | Simpson | 250/288 |
| 4,849,628 | 7/1989 | McLuckey et al. | 250/288 |

Primary Examiner—Jack I. Berman
Assistant Examiner—Kiet T. Nguyen
Attorney, Agent, or Firm—Zarley, McKee, Thomte, Voorhees & Sease

[57] ABSTRACT

An open-split interface includes a connector body having four leg members projecting therefrom within a single plane, the first and third legs being coaxial and the second and fourth legs being coaxial. A tubular aperture extends through the first and third legs and a second tubular aperture extends through the second and fourth legs, connecting at a juncture within the center of the connector body. A fifth leg projects from the connector body and has a third tubular aperture extending therethrough to the juncture of the first and second tubular apertures. A capillary column extends from a gas chromatograph into the third leg with its end adjacent the juncture. A flow restrictor tube extends from a mass spectrometer through the first tubular aperture in the first and third legs and into the capillary columnm end, so as to project beyond the end of the third leg within the capillary column. An annular gap between the tube and column allows excess effluent to pass to the juncture. A pair of short capillary columns extend from separate detectors into the second tubular aperture in the second and fourth legs, and are oriented with their ends spaced slightly from the first capillary column end. A sweep flow tube is mounted in the fifth leg so as to supply a helium sweep flow to the juncture.

10 Claims, 2 Drawing Sheets

OPEN-SPLIT INTERFACE FOR MASS SPECTROMETERS

TECHNICAL FIELD

The present invention relates generally to a device for connecting multiple detector inputs to a capillary gas chromatograph, and more particularly to an interface to connect a mass spectrometer and two other detectors to a capillary gas chromatograph while maintaining good chromatographic performance.

BACKGROUND OF THE INVENTION

Open-split interfacing conventionally utilizes a gas chromatography column with a flow restrictor connecting the column to a mass spectrometer. The gas chromatography (GC) column, must be at atmospheric pressure, and the mass spectrometer (MS) is operated at a high vacuum. A sweep gas must be introduced at the connection between the GC column and the MS to prevent the pumping of air into the MS. While open-split interfacing is known in the art, there are situations wherein immediate benefits would be obtained by connecting two other detectors with the mass spectrometer and capillary gas chromatograph. For example, in environmental gas chromatograph/mass spectrometer analyses, an electron capture detector could monitor chlorine, an NPD would monitor phosphorus, and the mass spectrometer would perform the traditional analyses.

It is therefore a general object of the present invention to provide an improved open-split interface for connecting a mass spectrometer and two other detectors with a capillary gas chromatograph.

Another object of the present invention is to provide an open-split interface for connecting a mass spectrometer with two other detectors in a capillary gas chromatograph which maintains good chromatographic performance.

A further object is to provide an open-split interface which utilizes two additional detectors on-line simultaneous and a mass spectrometer with a capillary gas chromatograph to increase reliability and accuracy of quantitative and qualitative analyses.

These and other objects of the present invention will be apparent to those skilled in the art.

SUMMARY OF THE INVENTION

The open-split interface of the present invention includes a connector body having first, second, third and fourth leg members lying within a single plane, the first and third legs being coaxial and the second and fourth legs being coaxial. A tubular aperture extends through the coaxial first and third legs and also through the coaxial second and fourth legs, connecting at a juncture within the center of the connector body. A fifth leg projects from the connector body and has a third tubular aperture extending therethrough to the juncture of the first and second tubular apertures. A capillary column end extends from a gas chromatograph into the third leg and is mounted with end lying in the juncture. A flow restrictor tube extends from a mass spectrometer through the first tubular aperture in the first and third legs and into the capillary column end, so as to project beyond the end of the third leg within the capillary column. The capillary column has an interior diameter greater than the exterior diameter of the flow restrictor tube so as to form an annular gap therebetween where they overlap. A pair of short capillary columns extend from separate detectors into the second and fourth legs, through the second tubular aperture and are oriented with their ends spaced slightly from the first capillary column end at the juncture in the connector body. A sweep flow tube is mounted in the fifth leg so as to supply a helium sweep flow to the juncture. Each of the columns, flow restrictor tube and flow tubes are sealably connected into their respective legs so as to prevent gas leaks.

DESCRIPTION OF THE PREFERRED EMBODIMENT

Figure 1:
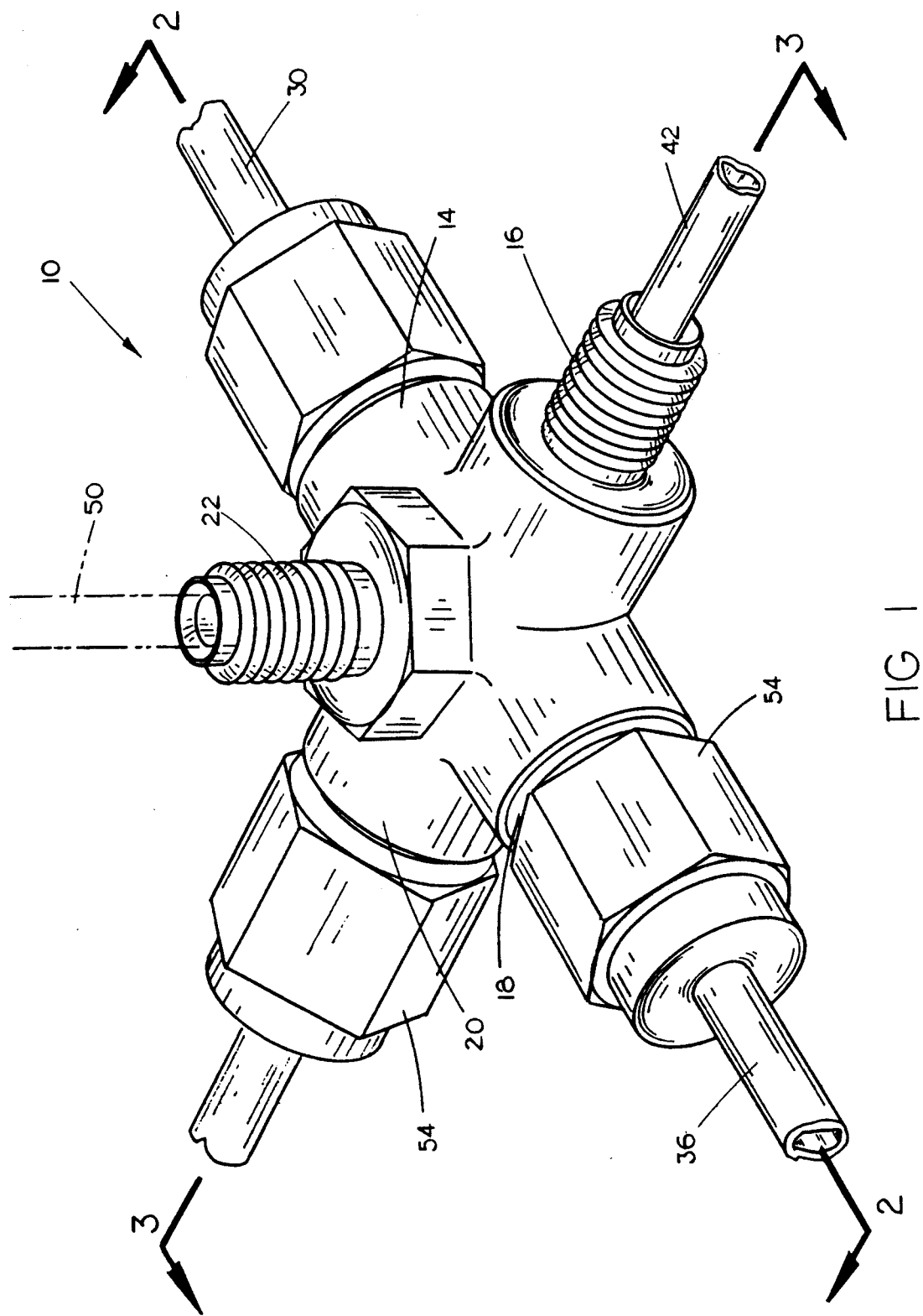
FIG. 1 is perspective view of the open-split interface connector of the present invention.

Referring now to the drawings, in which similar or corresponding parts are identified with the same reference numeral, and more particularly to FIG. 1, the open-split interface of the present invention is identified generally at 10 and includes a five-part cross tubing connector 12 having four legs 14, 16, 18 and 20 within a single plane, and a fifth leg 22 projecting perpendicularly from the plane of legs 14–20. Legs 14 and 18 extend coaxially, as do legs 16 and 20, the axis of each pair of legs crossing perpendicularly to form a cross with four perpendicular legs within the same plane.

Figure 2:
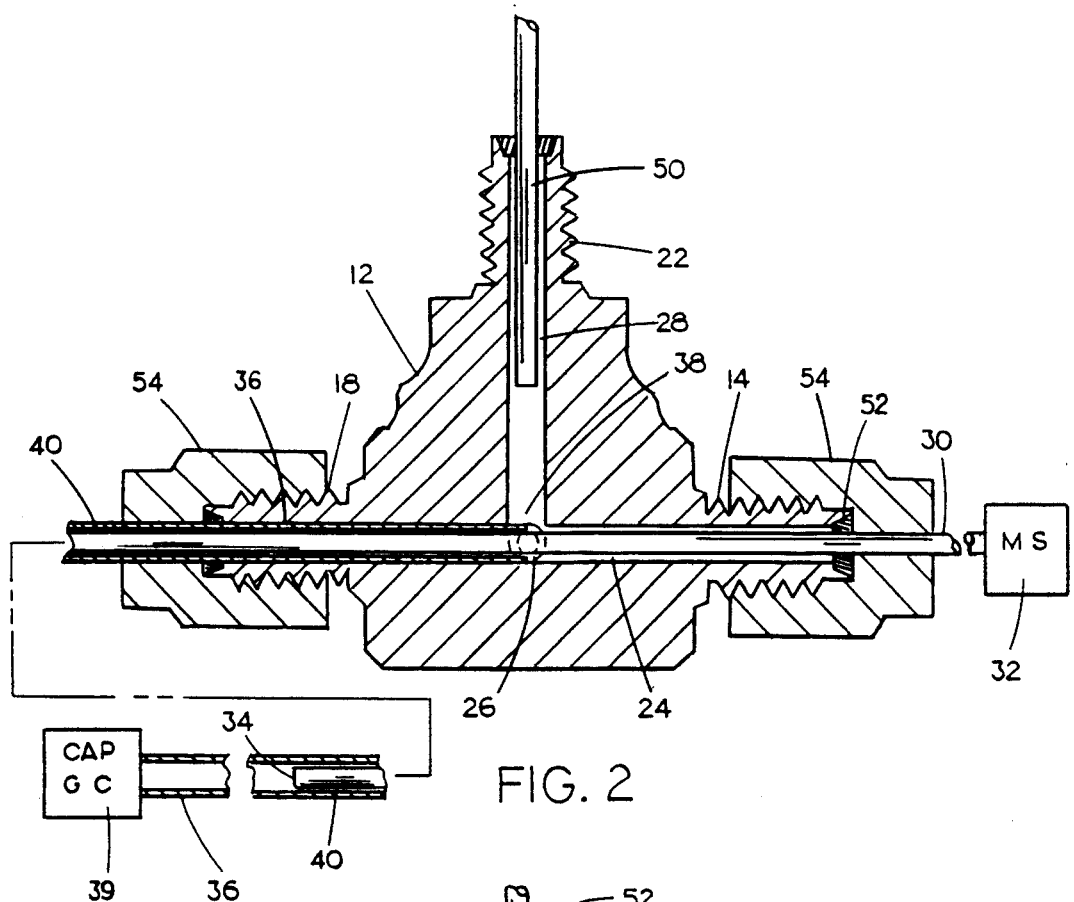
FIG. 2 is a sectional view through the connector taken at lines 2—2 in FIG. 1.
Figure 3:
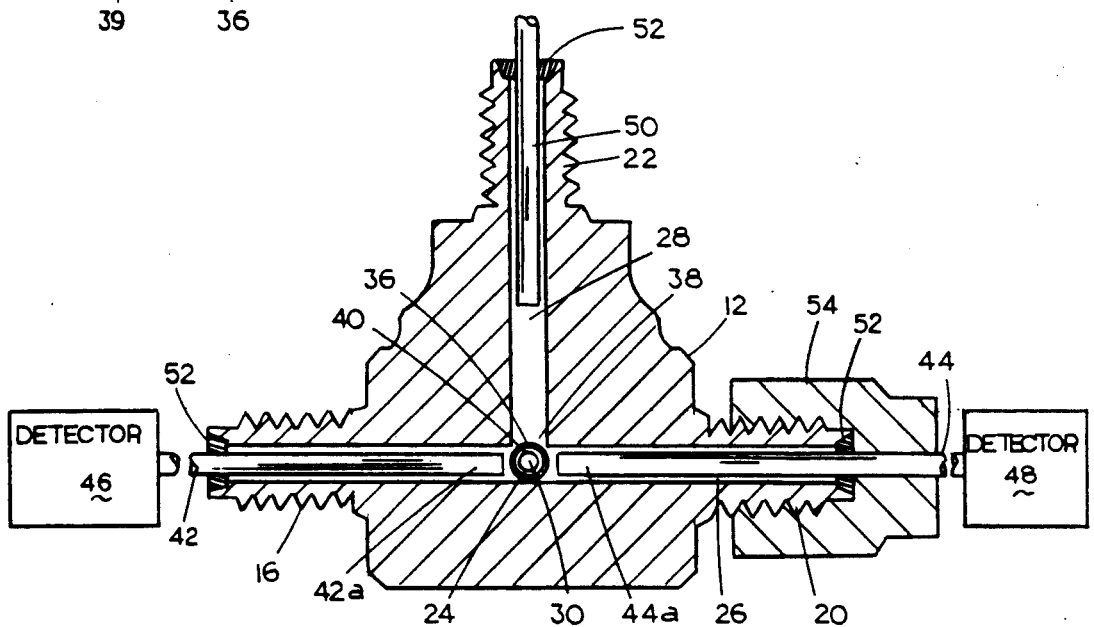
FIG. 3 is a sectional view taken at lines 3—3 in FIG. 1.

Referring now to FIG. 2, connector 12 has a tubular aperture 24 extending through legs 14 and 18 along their longitudinal axis. A second tubular aperture 26 extends through legs 16 and 20 and intersects tubular aperture 24 at the center of connector 12. A third tubular aperture 28 extends through leg 22 and intersects with tubular apertures 24 and 26 at the center of connector 12.

A hollow flow restrictor tube 30 connected to the high vacuum of a mass spectrometer 32 is journaled through first tubular aperture 24 through legs 14 and 18 and extends completely therethrough so as to project several centimeters beyond leg 18. Thus, intake port 34 of flow restrictor tube 30 projects from connector 12 out of leg 18. The column 36 extending from a capillary gas chromatograph 39 receives the intake end 34 of flow restrictor tube 30 and extends into leg 18 to the juncture 38 of tubular apertures 24, 26 and 28, within connector 12. The inner diameter of column 36 is greater than the outer diameter of flow restrictor tube 30 so as to form an annular space 40 therebetween extending to juncture 38.

Legs 16 and 20 of connector 12 each have a capillary column 42 and 44 respectively, extending therethrough to juncture 38. Capillary columns 42 and 44 are mounted with an approximate one millimeter gap between their intake ends 42a and 44a, respectively, and the end of gas chromatography column 36. Each capillary column 42 and 44 is connected to an atmospheric pressure-type detector 46 and 48, respectively.

A sweep flow tube 50 is inserted into third tubular aperture 28 in leg 22 and extends downwardly towards juncture 38. Sweep flow tube 50 is designed to provide a helium sweep flow to juncture 38, as described in more detail hereinbelow. All of the connections to connector 12 at legs 14, 16, 18, 20 and 22 are sealed with graphite/vespel ferrules 52 mounted in fittings 54, and each leg 14–22 is threaded so as to removably secure fittings 54 in a conventional fashion. A graphite/vespel ferrule is preferred since this type of ferrule will not leak air, nor will it crush the fused silica lines utilized in flow restrictor tube 30, column 36, and capillary columns 42 and 44. Sweep flow tube 50 is preferably stainless steel sealed with a stainless steel ferrule.

In operation, effluent from capillary gas chromatograph 39 flows through column 36 to juncture 38, at atmospheric pressure. Effluent from column 36, which is not carried by the flow restrictor tube 30 to the mass spectrometer 32, will exit in juncture 38 between capillary columns 42 and 44. A helium sweep flow is introduced into juncture 38 by sweep flow tube 50 and carries the excess effluent equally to detectors 46 and 48. Tests by the inventor have shown that two additional detectors may be added to a mass spectrometer and gas chromatograph, with the connector of this invention, while maintaining good chromatographic performance.

Whereas the invention has been shown and described in connection with the preferred embodiment thereof, it will be understood that many modifications, substitutions and additions may be made which are within the intended broad scope of the appended claims. Thus, there has been shown and described an improved open-split interface for mass spectrometers which accomplishes at least all of the above-stated objects.

I claim:

1. An open-split interface for mass spectrometers, comprising:
   a connector body having first, second, third and fourth leg members, said first and third legs being generally coaxial and said second and fourth legs being generally coaxial;
   a first tubular aperture extending through said connector body and said first and third legs;
   a second tubular aperture extending through said connector body and said second and fourth legs, connected with said first tubular aperture at a juncture within said connector body;
   a fifth leg projecting from said connector body;
   a third tubular aperture extending through said fifth leg to said juncture;
   means for sealably connecting a mass spectrometer to said first leg;
   means for sealably connecting a capillary gas chromatograph to said third leg;
   a first capillary column end extending from a gas chromatograph, connected to said third leg and extending through said first tubular aperture to said juncture;
   a flow restrictor tube extending from a mass spectrometer and journaled through said first tubular aperture in said first and third legs, said flow restrictor projecting beyond said third leg within said first capillary column end, said first capillary column having an interior diameter larger than said flow restrictor outside diameter, to form an annular gap therebetween;
   means for sealably connecting atmospheric pressure-type detectors to said second and fourth legs; and
   means for sealably connecting a sweep gas tube to said fifth leg.

2. The open-split interface of claim 1, further comprising:
   a second capillary column extending from an atmospheric pressure-type detector through said second tubular aperture into said second leg, to a point in said juncture adjacent and spaced from said first capillary column end in said third leg; and
   a third capillary column extending from an atmospheric pressure-type detector through said second tubular aperture into said fourth leg, to a point in said juncture adjacent and spaced from said first capillary column end in said third leg.

3. The open-split interface of claim 2, wherein said second and third capillary columns are each spaced approximately one millimeter from said first capillary column end.

4. The open-split interface of claim 3, further comprising a sweep gas flow tube mounted in said fifth leg and extending within said third tubular aperture.

5. The open-split interface of claim 1, wherein said means for connecting a capillary gas chromatograph to said third leg includes a selectively securable fitting having a ferrule means adapted to sealably connect said first capillary column to said third leg within said first tubular aperture.

6. The open-split interface of claim 1, wherein said means for connecting a mass spectrometer to said first leg includes a selectively securable fitting having a ferrule means adapted to sealably connect said flow restrictor tube to said first leg within said first tubular aperture.

7. The open-split interface of claim 2, wherein said means for connecting atmospheric pressure-type detectors to said second and fourth legs includes a selectively securable fitting having ferrule means adapted to sealably connect said second and third capillary columns to said second and fourth legs respectively within said second tubular aperture.

8. The open-split interface of claim 4, wherein said means for connecting a sweep gas tube to said fifth leg includes a selectively securable fitting having ferrule means adapted to sealably connect said sweep gas flow tube to said fifth leg within said third tubular aperture.

9. The open-split interface of claim 1, wherein said first, second, third and fourth legs lie within the same general plane, and said fifth leg projects generally perpendicularly therefrom.

10. The open-split interface of claim 9, wherein said first and third legs are oriented perpendicular to said second and fourth legs.

* * * * *